United States Patent [19]

Nakamura et al.

[11] Patent Number: 5,453,498
[45] Date of Patent: Sep. 26, 1995

[54] PROCESS FOR PRODUCTION OF HIGH-MONOESTER SUCROSE HIGHER FATTY ACID ESTERS

[75] Inventors: Shingo Nakamura, Kyoto; Hiroshi Nagahara, Shiga; Jun Kawaguchi, Osaka, all of Japan

[73] Assignee: Dai-Ichi Kogyo Seiyaku Co., Ltd., Kyoto, Japan

[21] Appl. No.: 12,090

[22] Filed: Feb. 1, 1993

[30] Foreign Application Priority Data

Feb. 12, 1992 [JP] Japan ............... 4-059357

[51] Int. Cl.⁶ ............... C07H 13/02; C07H 1/06
[52] U.S. Cl. ............... 536/119; 536/124; 536/127
[58] Field of Search ............... 536/119, 124, 536/127

[56] References Cited

U.S. PATENT DOCUMENTS

| | | | |
|---|---|---|---|
| 2,893,990 | 7/1959 | Hass et al. | 536/119 |
| 2,948,716 | 8/1960 | Davis | 536/119 |
| 2,999,858 | 9/1961 | Curtis | 536/119 |
| 3,053,830 | 9/1962 | Gaertner | 536/119 |
| 3,347,848 | 10/1967 | Imail et al. | 536/119 |
| 4,306,062 | 12/1981 | Jones | 536/119 |

FOREIGN PATENT DOCUMENTS

| | | | |
|---|---|---|---|
| 38-6165 | 5/1963 | Japan | 536/119 |
| 40-24606 | 10/1965 | Japan | 536/119 |
| 311092 | 1/1991 | Japan . | |

*Primary Examiner*—Michael G. Wityshyn
*Assistant Examiner*—Everett White
*Attorney, Agent, or Firm*—Jordan and Hamburg

[57] ABSTRACT

The invention relates to a method of producing a high-monoester sucrose higher fatty acid ester with a monoester content of at least 90%. In accordance with this invention, a sucrose higher fatty acid ester which is actually a mixture of the corresponding monoester, diester, triester, etc. is dissolved in 1 to 12 parts by weight of a solvent having a specific inductive capacity, at 25° C., of 30 to 50 at an elevated temperature, the precipitate formed on subsequent cooling is removed to recover a supernatant and the solvent is removed from the supernatant. In accordance with the invention, a high-monoester sucrose higher fatty acid ester can be produced easily and with good reproducibility.

5 Claims, No Drawings

PROCESS FOR PRODUCTION OF HIGH-MONOESTER SUCROSE HIGHER FATTY ACID ESTERS

BACKGROUND OF THE INVENTION

The present invention relates to a process for producing a high-monoester sucrose higher fatty acid ester (a higher fatty acid ester of sucrose with a high monoester content) which is of value as a solubilizer.

It is widely known that sucrose higher fatty acid esters are good food emulsifiers which are very safe and offer a broad range of HLB numbers ranging from high hydrophilicity to high lipophilicity according to the degree of esterification.

Particularly, sucrose higher fatty acid esters rich in monoester and diester components and, thus, having high HLB numbers are very effective emulsifiers for the formation of oil-in-water emulsions and it is also known that the monoesters have high solubilizing powers. However, the monoester content of the sucrose fatty acid esters commercially available today is generally not more than about 80%.

This is because of the following circumstances. The production technology heretofore used commercially for the production of a sucrose fatty acid ester involves a transesterification reaction between a fatty acid lower alcohol ester and sucrose (e.g. U.S. Pat. No. 2, 893,990), an acylation reaction between sucrose and a fatty acid halide or anhydride or an esterification reaction in the presence of an enzyme such as lipase. However, since 3 of the 8 hydroxyl groups of sucrose are primary and very reactive, it is difficult to selectively synthesize a monoester. Moreover, even if the starting material sucrose is used in large excess over the fatty acid, it is impossible to prevent production of the diester and triester.

Therefore, several procedures have been proposed for separating a sucrose higher fatty acid monoester from a mixture including the diester and triester.

By way of example, column chromatography or thin-layer chromatography using a halogenated hydrocarbon or methanol as the solvent and an extraction procedure using dimethylformamide, n-hexane, a halogenated hydrocarbon, methanol, water or the like as the solvent (e.g. Japanese Patent Publication No. 40-24606) are known.

However, the chromatographic method is disadvantageous in that it not only requires a large quantity of the solvent but is restricted in the batch size that can be treated. Regarding the extraction method, too, the use of n-hexane, a halogenated hydrocarbon or methanol presents a safety problem and particularly when methanol is used as the solvent, decomposition of the sucrose higher fatty acid ester by methanolysis is said to be unavoidable.

SUMMARY OF THE INVENTION

The object of the present invention is to overcome the above-mentioned disadvantages of the conventional technology and to provide a production process by which a high-monoester sucrose higher fatty acid ester having a monoester content of as high as 90% or more, which is of value as a solubilizer, can be produced from a sucrose higher fatty acid ester, which is actually a mixture of the monoester, diester, triester, etc., by an efficient extractive technique.

It has been found that, in accordance with this invention, the above object can be effectively accomplished, by employing a solvent having a defined specific inductive capacity in a defined range.

The method of the invention is characterized by dissolving a sucrose higher fatty acid ester in a solvent having a specific inductive capacity, at 25° C., of 30 to 50, the amount of said solvent being 1 to 12 parts by weight per part by weight of said sucrose higher fatty acid ester, at an elevated temperature, separating a supernatant from the precipitate formed on cooling, and removing the solvent from the supernatant.

The present invention utilizes the difference in solubility between a sucrose higher fatty acid ester monoester and the corresponding diester, triester, etc. in an extraction solvent. Since a sucrose higher fatty acid ester is an amphiphilic substance having both hydrophilic and lipophilic groups within its molecule, the above-mentioned desired effect can be obtained by employing a solvent having a specific inductive capacity in a defined range as the extraction solvent.

DESCRIPTION OF THE PREFERRED EMBODIMENTS

The solvent to be used in the present invention is preferably selected from the group consisting of water, ethanol, ethyl acetate, methyl ethyl ketone, dimethyl sulfoxide and isobutyl alcohol. Particularly, aqueous ethanol which is safe for ingestion is preferred. The specific inductive capacity values of these solvents are: water 78.5, ethanol 24.3, ethyl acetate 6.0, methyl ethyl ketone 19.0, dimethyl sulfoxide 49.5 and isobutyl alcohol 18.0. For use in accordance with the present invention, the solvent is adjusted to give a specific inductive capacity in the range of 30 to 50 at 25° C.

If the specific inductive capacity value is less than 30, the diester, triester, etc. do not separate out as a precipitate, so that the monoester cannot be effectively extracted specifically. However, it is not true that the monoester content of the product can be increased by merely raising the specific inductive capacity of the extraction solvent. If a highly polar solvent having a specific inductive capacity of over 50 is used, the monoester content of the extract is decreased to lower the product yield. This is probably because the excessively high polarity of the solvent lowers the solubility of the monoester.

The ratio of the solvent to the sucrose higher fatty acid ester is 1 to 12 parts by weight per part by weight of the ester. If the proportion of the solvent is less than 1 part by weight, the viscosity of the supernatant may increase or the precipitate may become viscous or paste-like depending on the species of fatty acid constituting the sucrose higher fatty acid ester and the species of the solvent used, with the result that the inter-separation of the supernatant and precipitate will be rendered difficult. If the proportion exceeds 12 parts by weight, it will become difficult to increase the monoester content of the product to 90% or higher and, in addition, a disadvantage will be felt in connection with the removal of the solvent.

The temperature to which the sucrose higher fatty acid ester dissolved by heating is cooled is preferably riot higher than 15° C.

There is no particular limitation on the species of sucrose higher fatty acid ester. However, in order to obtain a product suitable for use as a solubilizer, it is preferable to use a sucrose higher fatty acid ester whose fatty acid residue contains 8 to 22 carbon atoms. If the number of carbon atoms in the fatty acid residue is less than 8, the product will have only a moderate or weak solubilizing power. On the other hand, if the number of carbon atoms exceeds 22, the solubility in water will be decreased so that a product suitable for use as a solubilizer may not be obtained. It should, however, be understood that the fatty acid residue may be straight-chain or branched, or saturated or unsaturated.

The starting material sucrose higher fatty acid ester may be one that has been produced by any production process. For example, it may have been synthesized by whichever of the aforementioned transesterification reaction between a fatty acid lower alcohol ester and sucrose, acylation of sucrose with a fatty acid halide or anhydride, and esterification reaction with the aid of an enzyme.

In accordance with the present invention, a high-monoester sucrose higher fatty acid ester having a monoester content of as high as 90% or more can be produced using a solvent easy to handle, with good workability and high reproducibility. Furthermore, the product obtained by the method of the invention has an excellent solubilizing power and finds application in a broad range of uses.

The following examples are further illustrative of the invention. The sucrose higher fatty acid esters used as starting materials in the Examples and Comparative Examples were synthesized by the following processes.

Reference Example 1 (production of sucrose stearic acid ester)

In 4 l of dimethylformamide was dissolved 1 kg (2.93 mols) of sucrose at 90° C., followed by addition of 10 g of potassium carbonate and 600 g (2 mols) of methyl stearate, and the mixture was reacted under a reduced pressure of 70–90 mmHg at 90° C. for 3 hours. Then, 8 ml of acetic acid was added and the solvent was removed under reduced pressure. The residue was dissolved in 5 l of methyl ethyl ketone and the solution was washed with 3 portions of water. The methyl ethyl ketone was then removed under reduced pressure and the residue was recrystallized from acetone to provide 950 g of sucrose stearic acid ester.

Reference Example 2 (production of sucrose palmitic acid ester)

The procedure of Reference Example 1 was repeated except that 540 g (2 mols) of palmitate laurate was used in lieu of methyl stearate to provide 910 g of sucrose palmitic acid ester.

Reference Example 3 (production of sucrose lauric acid ester)

The procedure of Reference Example 1 was repeated except that 430 g (2 mols) of methyl laurate was used in lieu of methyl stearate to provide 810 g of sucrose lauric acid ester.

The ester compositions of the sucrose higher fatty acid esters prepared in Reference Examples 1 through 3 are shown in Table 1. The respective ester compositions were determined by gel chromatography.

TABLE 1

| | Ester composition of sucrose higher fatty acid ester (weight %) | | |
|---|---|---|---|
| | Reference Example 1 | Reference Example 2 | Reference Example 3 |
| Monoester | 63.8 | 66.0 | 68.7 |
| Diester | 30.7 | 28.8 | 26.3 |
| Triester | 5.0 | 5.2 | 5.0 |

Using the sucrose higher fatty acid esters prepared in Reference Examples 1 through 3, the following high-monoester sucrose higher fatty acid esters were produced.

EXAMPLE 1

In 500 g of 10% aqueous ethanol (specific inductive capacity=30, 25° C.) was dissolved 100 g of the sucrose stearic acid ester of Reference Example 1 at an elevated temperature of 35°–45° C. This solution was cooled with ice and the upper liquid layer was separated by decantation. From this layer, the solvent was removed under reduced pressure to provide 20 g of sucrose stearic acid monoester.

EXAMPLE 2

In 1000 g of 15% aqueous ethanol (specific inductive capacity=32, 25° C.) was dissolved 100 g of the sucrose palmitic acid ester of Reference Example 2 at an elevated temperature of 35°–45° C. The solution was cooled with ice and the upper liquid layer was separated by decantation. From this layer, the solvent was distilled off to provide 55 g of sucrose palmitic acid monoester.

EXAMPLE 3

In 500 g of 40% aqueous ethanol (specific inductive capacity=46, 25° C.) was dissolved 100 g of the sucrose lauric acid ester of Reference Example 3 at an elevated temperature of 35°–45° C. This solution was cooled with ice and the upper liquid layer was separated by decantation. From this layer, the solvent was removed under reduced pressure to provide 38 g of sucrose lauric acid monoester.

EXAMPLE 4

In 500 g of a solvent system composed of 50% dimethyl sulfoxide, 30% methyl ethyl ketone and 20% ethanol (specific inductive capacity=35, 25° C.) was dissolved 100 g of the sucrose stearic acid ester of Reference Example 1 at an elevated temperature of 35°–45° C. This solution was cooled with ice and the upper liquid layer was separated by decantation. From this layer, the solvent was removed under reduced pressure to provide 16 g of sucrose stearic acid monoester.

EXAMPLE 5

In 500 g of a solvent system composed of 30% $H_2O$ 40% isobutyl alcohol and 30% ethanol (specific inductive capacity=38, 25° C.) was dissolved 100 g of the sucrose stearic acid ester of Reference Example 1 at an elevated temperature of 50°–55° C. This solution was cooled with ice and the upper liquid layer was separated by decantation. From this layer, the solvent was removed under reduced pressure to provide 17 g of sucrose stearic acid monoester.

EXAMPLE 6

In 500 g of a solvent system composed of 40% $H_2O$ 30% ethyl acetate and 30% ethanol (specific inductive capacity=40, 25° C.) was dissolved 100 g of the sucrose stearic acid ester of Reference Example 1 at an elevated temperature of 50°–60° C. This solution was cooled with ice and the upper liquid layer was separated by decantation. From this layer, the solvent was removed under reduced pressure to provide 17 g of sucrose stearic acid monoester.

Comparative Example 1

In 500 g of ethanol (specific inductive capacity=24.3, 25° C.) was dissolved 100 g of the sucrose stearic acid ester of Reference Example 1 at an elevated temperature of 70° C. This solution was cooled with ice but no precipitate was formed. Therefore, the monoester could not be fractionally separated.

Comparative Example 2

In 500 g of 5% aqueous ethanol (specfic inductive capacity=27, 25° C.) was dissolved 100 g of the sucrose stearic acid ester of Reference Example 1 at an elevated temperature of 35°–45° C. This solution was cooled with ice but no precipitate was formed. Therefore, the monoester could not be fractionally separated.

Comparative Example 3

In 1500 g of 15% aqueous ethanol (specific inductive capacity=32, 25° C.) was dissolved 100 g of the sucrose palmitic acid ester of Reference Example 2 at an elevated temperature of 35°–45° C. This solution was cooled with ice and the upper liquid layer was separated by decantation. From this layer, the solvent was removed under reduced pressure to provide 58 g of sucrose palmitic acid ester.

Comparative Example 4

In 500 g of 45% aqueous ethanol (specific inductive capacity=51, 25° C.) was dissolved 100 g of the sucrose lauric acid ester of Reference Example 3 at an elevated temperature of 35°–45° C. This solution was cooled with ice and the upper liquid layer was separated by decantation. From this layer, the solvent was removed under reduced pressure to provide 20 g of sucrose lauric acid ester.

Comparative Example 5

In 500 g of ethyl acetate (specific inductive capacity=6, 25° C.) was dissolved 100 g of the sucrose stearic acid ester of Reference Example 1 at an elevated temperature of 50°–60° C. This solution was cooled with ice but no precipitate was formed. Therefore, the monoester could not be fractionally separated.

Comparative Example 6

In 500 g of methyl ethyl ketone (specific inductive capacity=19, 25° C.) was dissolved 100 g of the sucrose stearic acid ester of Reference Example 1 at an elevated temperature of 35°–45° C. This solution was cooled with ice but no precipitate was formed. Therefore, the monoester could not be fractionally separated.

Comparative Example 7

In 500 g of isobutyl alcohol (specific inductive capacity=18, 25° C.) was dissolved 100 g of the sucrose stearic acid ester of Reference Example 1 at an elevated temperature of 50°–60° C. This solution was cooled with ice but no precipitate was formed. Therefore, the monoester could not be fractionally separated.

Comparative Example 8

In 500 g of a solvent system composed of 50% $H_2O$ and 50% dimethyl sulfoxide (specific inductive capacity=64, 25° C.) was dissolved 100 g of the sucrose stearic acid ester of Reference Example 1 at an elevated temperature of 50°–60° C. This solution was cooled with ice and the upper liquid layer was separated by decantation. From this layer, the solvent was removed under reduced pressure to provide 15 g of sucrose stearic acid ester.

The ester compositions and yields of the products obtained in the above Examples and Comparative Examples are presented in Table 2. The ester compositions were determined by gel chromatography.

TABLE 2

| | Fatty acid constituting the sucrose higher fatty acid ester | Extraction solvent | | Ratio of solvent to starting material | Ester composition (wt. %) | | Yield based on starting material (%) |
|---|---|---|---|---|---|---|---|
| | | Solvent species and ratio (%) | Specific inductive capacity at 25° C. | | Monoester | Diester | |
| Example | | | | | | | |
| 1 | Stearic acid | $H_2O$ 10<br>Ethanol 90 | 30 | ×5 | 98.2 | 1.8 | 20 |
| 2 | Palmitic acid | $H_2O$ 15<br>Ethanol 85 | 32 | ×10 | 96.8 | 3.2 | 55 |
| 3 | Lauric acid | $H_2O$ 40<br>Ethanol 60 | 46 | ×5 | 92.1 | 7.9 | 38 |
| 4 | Stearic acid | DMSO 50<br>MEK 30<br>Ethanol 20 | 35 | ×5 | 97.3 | 2.7 | 16 |
| 5 | Stearic acid | $H_2O$ 30<br>Isobutyl alcohol 40<br>Ethanol 30 | 38 | ×5 | 98.0 | 2.0 | 17 |
| 6 | Stearic acid | $H_2O$ 40 | 43 | ×5 | 97.4 | 2.6 | 17 |

TABLE 2-continued

| Fatty acid constituting the sucrose higher fatty acid ester | Extraction solvent | | | Ester composition (wt. %) | | Yield based on starting material (%) |
| | Solvent species and ratio (%) | Specific inductive capacity at 25° C. | Ratio of solvent to starting material | Monoester | Diester | |
|---|---|---|---|---|---|---|
| | Ethyl acetate 30 | | | | | |
| | Ethanol 30 | | | | | |
| Comparative Example | | | | | | |
| 1 | Stearic acid | Ethanol | 24.3 | ×5 | — | — | — |
| 2 | Stearic acid | H₂O 5 / Ethanol 95 | 27 | ×5 | — | — | — |
| 3 | Palmitic acid | H₂O 15 / Ethanol 85 | 32 | ×15 | 87.0 | 13.0 | 58 |
| 4 | Lauric acid | H₂O 45 / Ethanol 55 | 51 | ×5 | 85.0 | 15.0 | 20 |
| 5 | Stearic acid | Ethyl acetate | 6 | ×5 | — | — | — |
| 6 | Stearic acid | MEK | 19 | ×5 | — | — | — |
| 7 | Stearic acid | Isobutyl alcohol | 18 | ×5 | — | — | — |
| 8 | Stearic acid | H₂O 50 / DMSO 50 | 64 | ×5 | 72.0 | 28.0 | 15 |

Note) DMSO stands for dimethyl sulfoxide and MEK stands for methyl ethyl ketone.

The solubilizing powers of the products according to the above examples for Orange OT (an oil-soluble dye; 1-[(2-methylphenyl)azo]-2-naphthalenol) were determined by the dye solubilizing assay method. The results are presented in Table 3.

Dye solubilizing assay

Orange OT is added to an aqueous solution of each sucrose higher fatty acid monoester and the mixture is shaken until a solubilization equilibrium is established. Then, the excess dye which could not be solubilized is removed by centrifugation and the absorbance of the supernatant is measured at 497 nm, the maximum absorption wavelength of Orange OT, to calculate the amount of solubilized Orange OT.

For comparison, similar determinations were performed using the sucrose stearic acid ester used as the starting material in Example 1 (monoester content 63.8 weight %), the sucrose lauric acid ester obtained in Comparative Example 4 (monoester content 85.0 weight %) the sucrose stearic acid ester obtained in Comparative Example 8 (monoester content 72.0 weight %), polyoxyethylene-hydrogenated castor oil 60 (Nippon Surfactant Industry) which is in broad use as a pharmaceutical solubilizer and Polysorbate 80 (Dai-Ichi Kogyo Seiyaku Co., Ltd) which is also a routine pharmaceutical solubilizer. The results are presented in Table 3.

TABLE 3

| Solubilizer | Monoester content (wt. %) | Amount of solubilized Orange OT (mg/l) |
|---|---|---|
| Product of Example 1 | 98.2 | 150.5 |
| Product of Example 2 | 96.8 | 120.5 |
| Product of Example 3 | 92.1 | 51.8 |
| Product of Example 4 | 97.3 | 138.8 |
| Product of Example 5 | 98.0 | 146.0 |
| Product of Example 6 | 97.4 | 139.0 |
| Starting material in Example 1 | 63.8 | —*¹ |
| Product of Comparative Example 4 | 85.0 | 3.3 |
| Product of Comparative Example 8 | 72.0 | —*¹ |
| Polyoxyethylene-hydrogenated castor oil 60 | — | 162.2 |
| Polysorbate 80 | — | 39.9 |

*¹: The solution developed white turbidity, preventing determination.

It is apparent from Table 3 that the high-monoester sucrose higher fatty acid esters obtainable by the method of the invention have very remarkable solubilizing powers.

What is claimed is:

1. A process for producing a high-monoester sucrose higher fatty acid ester having a monoester content of not less than 90% which comprises:

dissolving a sucrose higher fatty acid ester in a solvent at a temperature as low as 35° C. to a temperature as high as 60° C.;

said solvent containing at least one of ethyl acetate and dimethyl surfoxide and being adjusted to give a specific inductive capacity, at 25° C., of 30 to 50, the amount of said solvent being 1 to 12 parts by weight based on each part by weight of said sucrose higher fatty acid ester;

separating a supernatant after cooling; and removing said solvent from said supernatant.

2. A process as claimed in claim 1, wherein said solvent further comprises at least one species selected from the group consisting of water, ethanol, methyl ethyl ketone, and isobutyl alcohol.

3. A process as claimed in claim 1, wherein said solvent further comprises aqueous ethanol.

4. A process as claimed in claim 1, wherein the fatty acid residue of said sucrose higher fatty acid ester contains 8 to 22 carbon atoms.

5. A process as claimed in claim 1, wherein said supernatant is separated by decantation.

* * * * *